(12) United States Patent
Takemoto et al.

(10) Patent No.: US 10,980,500 B2
(45) Date of Patent: Apr. 20, 2021

(54) MOBILE RADIOGRAPHIC IMAGING APPARATUS

(71) Applicant: Shimadzu Corporation, Kyoto (JP)

(72) Inventors: Hajime Takemoto, Kyoto (JP); Toru Hayakawa, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 16/486,105

(22) PCT Filed: Nov. 21, 2017

(86) PCT No.: PCT/JP2017/041798
§ 371 (c)(1),
(2) Date: Aug. 14, 2019

(87) PCT Pub. No.: WO2018/150668
PCT Pub. Date: Aug. 23, 2018

(65) Prior Publication Data
US 2020/0229779 A1 Jul. 23, 2020

(30) Foreign Application Priority Data
Feb. 15, 2017 (JP) .............................. JP2017-025844

(51) Int. Cl.
*H05G 1/02* (2006.01)
*A61B 6/00* (2006.01)

(52) U.S. Cl.
CPC ............ *A61B 6/4405* (2013.01); *A61B 6/447* (2013.01); *A61B 6/4452* (2013.01)

(58) Field of Classification Search
CPC ...... A61B 6/4405; A61B 6/4452; A61B 6/447; A61B 6/00
See application file for complete search history.

(56) References Cited

U.S. PATENT DOCUMENTS 3,575,368 A * 4/1971 Thomas ............... F16M 11/046
248/572
2016/0199013 A1 7/2016 Moreno Vallejo et al.

FOREIGN PATENT DOCUMENTS

| CA | 2877381 A1 * | 1/2015 | ............ A61B 6/447 |
|---|---|---|---|
| EP | 2859849 A1 | 4/2015 | |
| JP | S56-043893 U | 4/1981 | |
| JP | 2004-33415 A | 2/2004 | |
| JP | 2016-526425 A | 9/2016 | |

OTHER PUBLICATIONS

International Search Report for PCT application PCT/JP2017/041798, submitted with a machine translation.

* cited by examiner

*Primary Examiner* — Kiho Kim
(74) *Attorney, Agent, or Firm* — Muir Patent Law, PLLC

(57) ABSTRACT

The axial direction B of the spindle 64 for supporting the movable pulleys 58 and 59 is arranged at a position rotated about the axis of the shaft relative to the axial direction of the spindle 56. The axial direction B of the spindle 64 is arranged in a state of being inclined by a predetermined angle with respect to the axial direction A when the movable pulleys 58 and 59 are in the lifted position. This allows the movable pulleys 58 and 59 to be automatically moved to a position at which no stress is applied to the first wire rope 54.

6 Claims, 11 Drawing Sheets

MOBILE RADIOGRAPHIC IMAGING APPARATUS

TECHNICAL FIELD

The present invention relates to a mobile radiographic imaging apparatus.

BACKGROUND ART

A mobile X-ray imaging apparatus, which is a kind of mobile radiographic imaging apparatus, is also referred to as an X-ray imaging apparatus for rounds, and performs X-ray imaging by moving between hospital rooms. This mobile X-ray imaging apparatus is provided with a main body having front wheels and rear wheels, a support column erected on the main body, a lifting and lowering member that moves upward and downward along the support column in a state of supporting an X-ray irradiation unit composed of an X-ray tube and a collimator, an X-ray detector that detects X-rays emitted from the X-ray irradiation unit and passed through the subject, and a battery disposed inside the main body.

In such a mobile X-ray imaging apparatus, it is necessary to lift and lower the X-ray irradiation unit composed of an X-ray tube and a collimator depending on the situation of imaging. At this time, since the X-ray irradiation unit has a large weight, a lifting and lowering assist mechanism is adopted in order to facilitate lifting and lowering of the X-ray irradiation unit. As this lifting and lowering assist mechanism, conventionally, a lifting and lowering assist mechanism is used in which an X-ray irradiation unit is connected to one end of a wire rope wound around a fixed pulley and a counterweight having a weight similar to that of the X-ray irradiation unit is connected the other end of the wire rope. However, this lifting and lowering assist mechanism has a problem that the weight of the entire device is increased since it uses a counterweight having the similar weight as that of the X-ray irradiation unit in addition to the X-ray irradiation unit. For this reason, a lifting and lowering assist mechanism using a spring instead of a counterweight has been proposed.

In the lifting and lowering assist mechanism using a spring, in order to cope with the change of the urging force due to the extension and contraction of the spring, the configuration using a pulley (pulley) in which the winding radius of the wire rope changes according to the rotation angle is adopted. That is, in Patent Document 1, a mobile X-ray device is disclosed in which a lifting and lowering assist mechanism using a cone pulley on which a spiral groove is formed is used. Further, in Patent Document 2, a mobile X-ray device equipped with a variable radius pulley is disclosed.

PRIOR ART

Patent Document

Patent Document 1: Japanese Unexamined Patent Application Publication No. 2004-33415
Patent Document 2: European Unexamined Patent Application Publication No. 2859849

SUMMARY OF THE INVENTION

Problems to be Solved by the Invention

When using a spiral cone pulley in which a winding radius of a wire rope changes in accordance with the rotation angle changes as described in Patent Document 1 and Patent Document 2, the position at which the wire rope is separated from the surface of the spiral cone pulley moves in the axial direction of the spiral cone pulley as the rotation angle position of the spiral cone pulley changes. For this reason, in the configuration in which the wire rope is wound around other pulleys, the stress in the twist direction is applied to the wire rope, which causes a problem of shortening the life of the wire rope.

The present invention has been made to solve the aforementioned problems, and aims to provide a mobile radiographic imaging apparatus capable of preventing shortening of a life of a wire rope by preventing a stress in a twist direction from being applied to the wire rope even in the case of using a spiral cone pulley in which a winding radius of the wire rope changes in accordance with a rotation angle.

Means for Solving the Problems

According to the invention as recited in claim 1, a mobile radiographic imaging apparatus is provided with a main body with wheels, a support column erected on the main body, and a lifting and lowering member configured to be lifted and lowered along the support column in a state of supporting the radiation irradiation portion. The radiographic imaging apparatus includes: a spiral cone pulley in which a winding radius of a wire rope changes depending on a rotation angle, the spiral cone pulley being provided at an upper portion of the support column in a rotatable manner; a movable pulley; a wire rope wound around the movable pulley and the spiral cone pulley with one end of the wire rope fixed to the support column and the other end thereof fixed to the spiral cone pulley; a movable pulley holder configured to support a rotary spindle of the movable pulley; a spring configured to apply tension to the wire rope; a coupling mechanism configured to couple the movable pulley holder with the spring in a manner as to be rotatable about an axis facing a central axis direction of the spring; and a lifting and lowering drive mechanism configured to lift and lower the lifting and lowering member by rotation of the spiral cone pulley.

According to the invention as recited in claim 2, in the invention as recited in claim 1, the movable pulley holder is configured to be tiltable with respect to an axis facing the central axis direction of the spring.

According to the invention as recited in claim 3, in the invention as recited in claim 1, the lifting and lowering drive mechanism includes: a winding pulley that rotates in synchronization with the spiral cone pulley; a second wire rope wound around the winding pulley with one end of the second wire rope fixed to the winding pulley and the other end thereof fixed to the lifting and lowering member.

According to the invention as recited in claim 4, in the invention as recited in any one of claims 1 to 3, the spring is a compression coil spring with an upper end fixedly in contact with an upper spring seat provided at a holding member, and the coupling mechanism is provided with a shaft that couples a lower spring seat in contact with a lower end of the compression coil spring and the movable pulley holder.

Effects of the Invention

According to the invention as recited in claim 1, it is possible to automatically move the rotation angle position of the movable pulley about an axis facing the central axis direction of the spring to a position where no stress is applied to the wire rope. This makes it possible to reduce the stress applied to the wire rope, which in turn can prevent the shortening of the life of the wire rope.

According to the invention as recited in claim 2, it is possible to automatically move the inclination angle position of the movable pulley with respect to the axis facing the central axis direction of the spring to a position where no stress is applied to the wire rope. This makes it possible to further reduce the stress applied to the wire rope, which in turn can prevent the shortening of the life of the wire rope.

According to the invention as recited in claim 3, even with a simple configuration using the winding pulley and the second wire rope, it is possible to easily lift and lower the lifting and lowering member by utilizing the rotation of the spiral cone pulley.

According to the invention as recited in claim 4, since the compression coil spring is used, it is possible to prevent the lifting and lowering member from lowing by a large distance together with the radiation irradiation portion even when the spring is broken.

EMBODIMENTS FOR CARRYING OUT THE INVENTION

Figure 1:
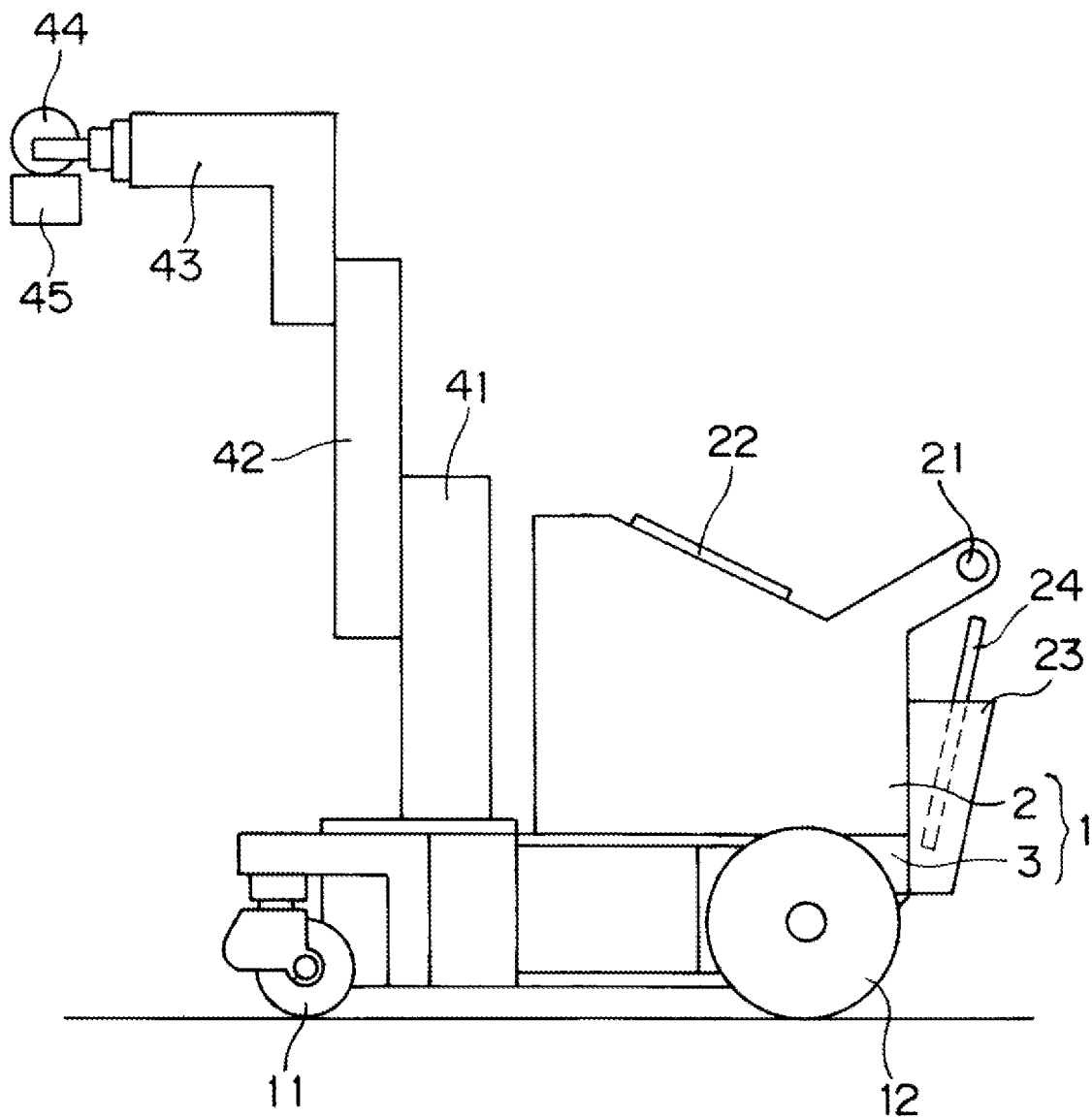
FIG. 1 is a schematic diagram of a mobile X-ray imaging apparatus as a mobile radiographic imaging apparatus according to the present invention.

Hereinafter, embodiments of the present invention will be described with reference to the drawings. FIG. 1 is a schematic diagram of a mobile X-ray imaging apparatus as a mobile radiographic imaging apparatus according to the present invention.

This mobile X-ray imaging apparatus is also referred to as an X-ray imaging apparatus for rounds for performing X-ray imaging by moving between hospital rooms, and is provided with a main body 1 composed of a body 2 and a chassis 3. On the front side in the traveling direction of the chassis 3 in this mobile X-ray imaging apparatus, a pair of left and right front wheels 11 which are wheels for changing the direction is provided. Further, on the rear side in the traveling direction of the chassis 3 in this mobile X-ray imaging apparatus, a pair of left and right rear wheels 12 which are driving wheels is provided.

On the front side of the chassis 3 constituting the main body 1 in the traveling direction, a support column 41 is erected. A first lifting and lowering member 42 and a second lifting and lowering member 43 are provided to the support column 41 in a vertically movable manner. The second lifting and lowering member 43 has a substantially L-shape in a side view, and is provided with, at its tip end, an X-ray irradiation unit composed of an X-ray tube 44 and a collimator 45. The first lifting and lowering member 42 and the second lifting and lowering member 43 constitute the lifting and lowering member according to the present invention, and the X-ray tube 44 and the collimator 45 are lifted and lowered in accordance with the lifting and lowering operations of the first lifting and lowering member 42 and the second lifting and lowering member 43. The support column 41 is supported rotatably about the vertical axis, and the X-ray tube 44 and the collimator 45 turn together with the second lifting and lowering member 43 as the support column 41 rotates.

The body 2 constituting the main body 1 is provided with an operation handle 21 for operating the traveling direction of the main body 1, an LCD touch panel 22 functioning as a display unit and an operation unit, and a storage portion 23 for storing an X-ray detector 24, such as, e.g., a flat panel detector for detecting X-rays irradiated from the X-ray tube 44 and passed through a subject.

Figure 2:
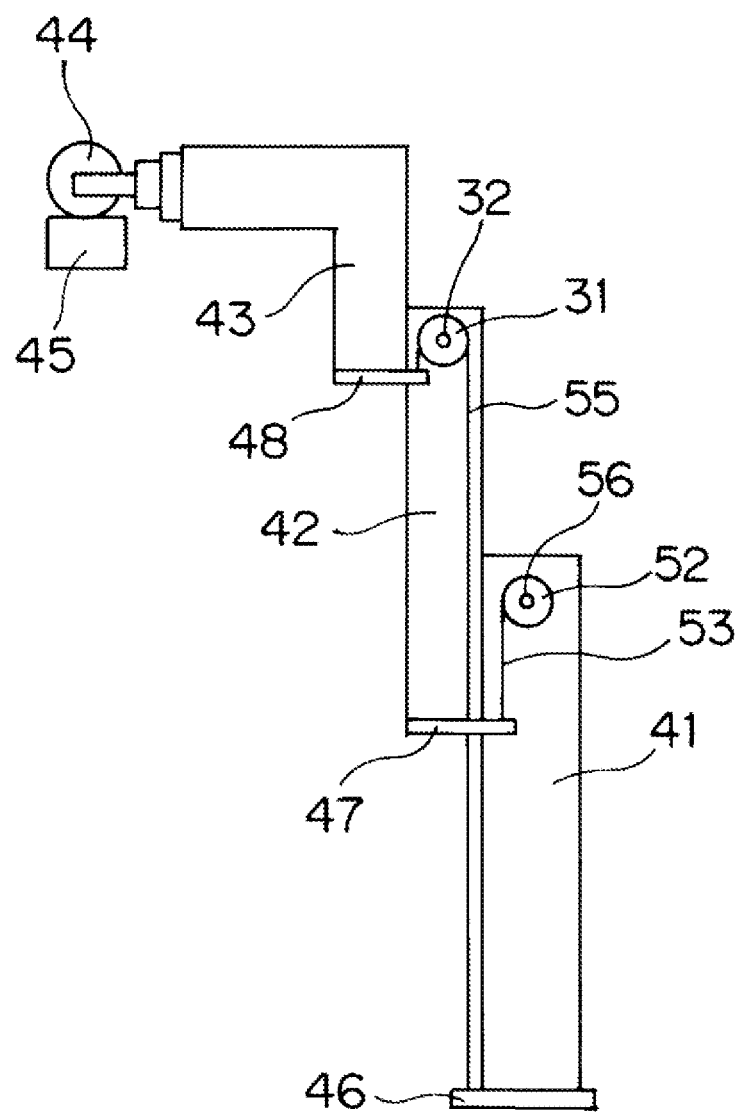
FIG. 2 is a schematic side diagram showing a lifting and lowering mechanism of a first lifting and lowering member 42 and a second lifting and lowering member 43.
Figure 3:
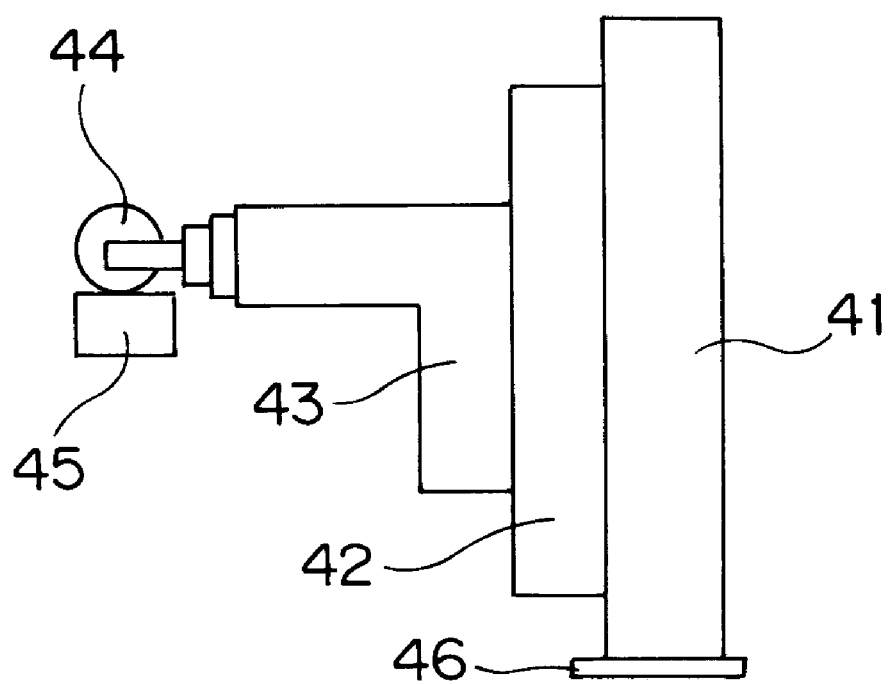
FIG. 3 is a schematic side view showing a lifting and lowering state of the first lifting and lowering member 42 and the second lifting and lowering member 43.
Figure 4:
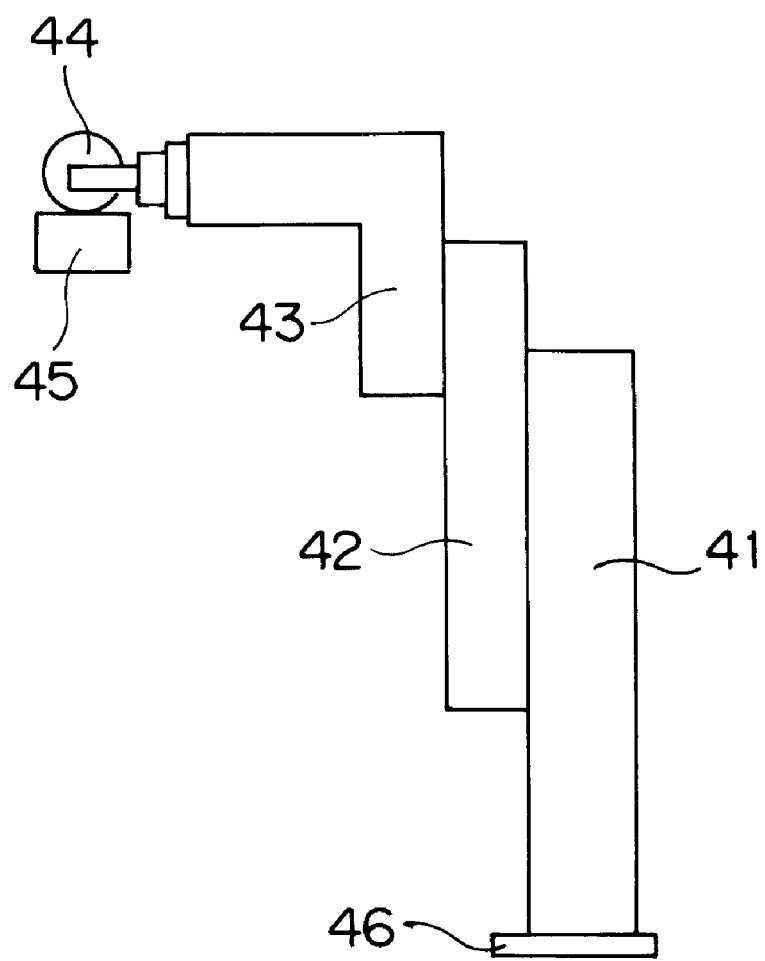
FIG. 4 is a schematic side view showing a lifting and lowering state of the first lifting and lowering member 42 and the second lifting and lowering member 43.

First, the lifting and lowering operations of the first lifting and lowering member 42 and the second lifting and lowering member 43 will be described. FIG. 2 is a schematic side diagram showing the lifting and lowering mechanism of the first lifting and lowering member 42 and the second lifting and lowering member 43. FIG. 3 and FIG. 4 are side views showing the lifting and lowering states of the first lifting and lowering member 42 and the second lifting and lowering member 43. FIG. 3 shows a state in which the first lifting and lowering member 42 and the second lifting and lowering member 43 are lowered, and FIG. 4 shows a state in which the first lifting and lowering member 42 and the second lifting and lowering member 43 are lifted.

The first lifting and lowering member 42 can be lifted and lowered along the support column 41 by a guide member (not shown) provided to the support column 41. The second lifting and lowering member 43 can be lifted and lowered along the first lifting and lowering member 42 together with the X-ray tube 44 and the collimator 45 by a guide member (not shown) provided to the first lifting and lowering member 42.

As shown in FIG. 2, at the upper portion of the support column 41, a winding pulley 52 described later is provided rotatably about a spindle 56 fixed to the upper portion of the support column 41. A second wire rope 53 is wound around the winding pulley 52 with one end fixed to the winding pulley 52 and the other end fixed to a base portion 47 provided at the lower end portion of the first lifting and lowering member 42. For this reason, when the winding pulley 52 rotates and the winding amount of the second wire rope 53 with respect to the winding pulley 52 changes, the first lifting and lowering member 42 is lifted and lowered.

On the other hand, as shown in FIG. 2, at the upper portion of the first lifting and lowering member 42, a fixed pulley 31 is provided rotatably about a support spindle 32 fixed at the upper portion of the first lifting and lowering member 42. A wire rope 55 for the second lifting and lowering member 43 is wound around the fixed pulley 31 with one end fixed to the base portion 46 provided to the lower end portion of the support column 41 and the other end fixed to a base portion 48 provided to the lower end portion of the second lifting and lowering member 43. For this reason, when the wire rope 55 is unwound to the base portion 46 side in accordance with the lifting of the first lifting and lowering member 42 by the action of the second wire rope 53, the second lifting and lowering member 43 also is lifted with respect to the first lifting and lowering member 42. On the other hand, when the wire rope 55 is unwound to the base portion 48 side in accordance with the lowering of the first lifting and lowering member 42, the second lifting and lowering member 43 also is lowered with respect to the first lifting and lowering member 42.

For this reason, when the first lifting and lowering member 42 is lifted in accordance with the rotating of the winding pulley 52, as shown in FIG. 4, the second lifting and lowering member 43 is lifted together with the X-ray irradiation unit composed of the X-ray tube 44 and the collimator 45 two times as much as the lifting amount of the first lifting and lowering member 42. When the first lifting and lowering member 42 is lowered in accordance with the rotating of the winding pulley 52, as shown in FIG. 3, the second lifting and lowering member 43 is lowered together with the X-ray irradiation unit composed of the X-ray tube 44 and the collimator 45 two times as much as the lowering amount of the first lifting and lowering member 42. Note that when the support column 41 rotates about the axis facing in the vertical direction with respect to the chassis 3 constituting the main body 1, the X-ray irradiation unit composed of the X-ray tube 44 and the collimator 45 is turned together with the second lifting and lowering member 43.

Figure 5:
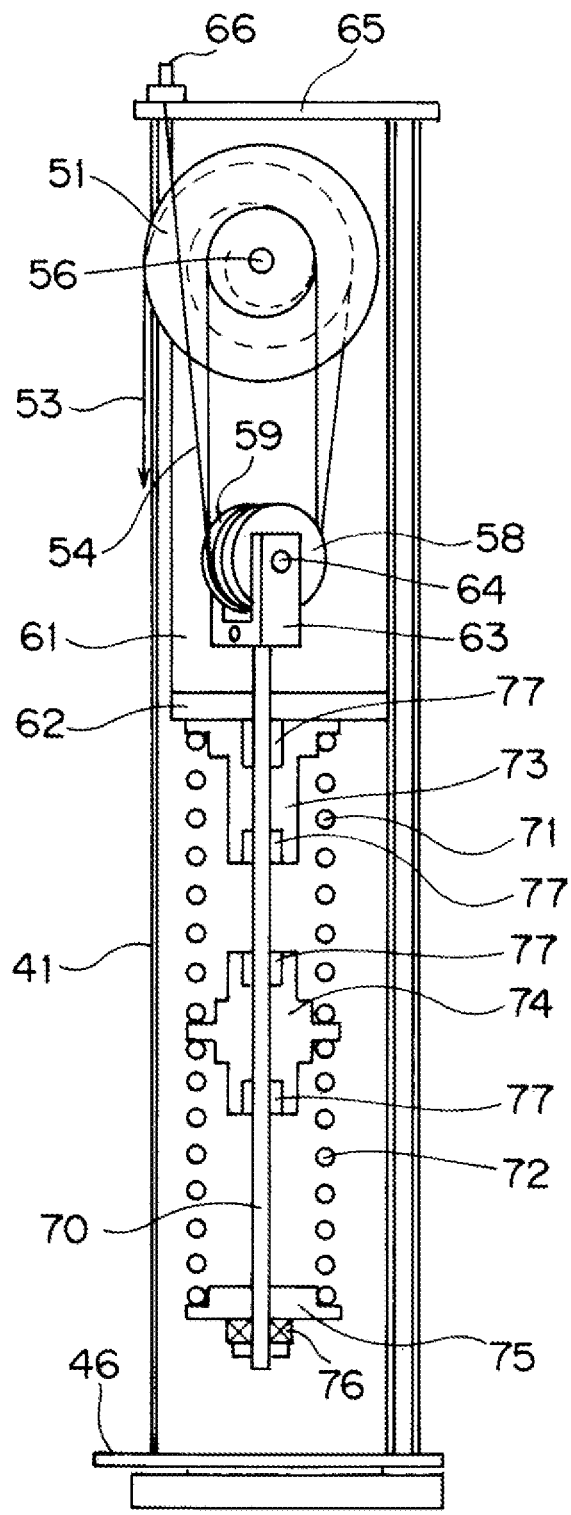
FIG. 5 is a side view of the lifting and lowering assist mechanism.
Figure 6:
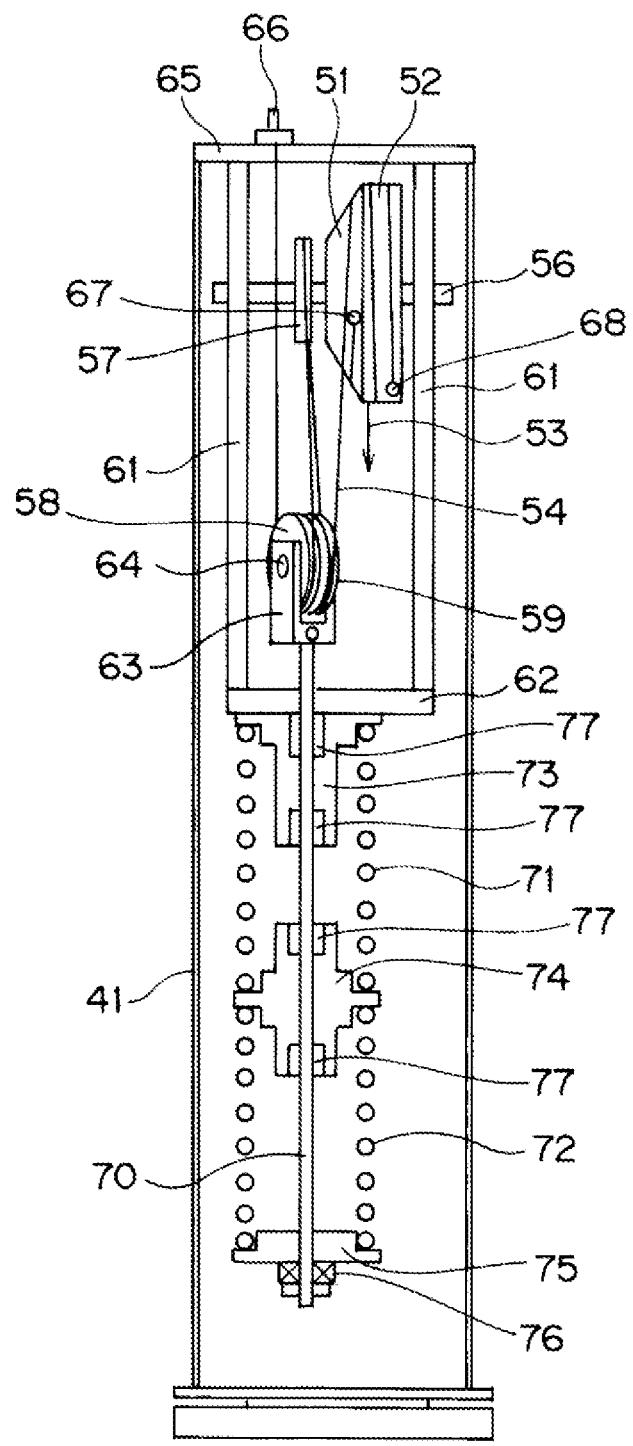
FIG. 6 is a front view of the lifting and lowering assist mechanism.
Figure 7:
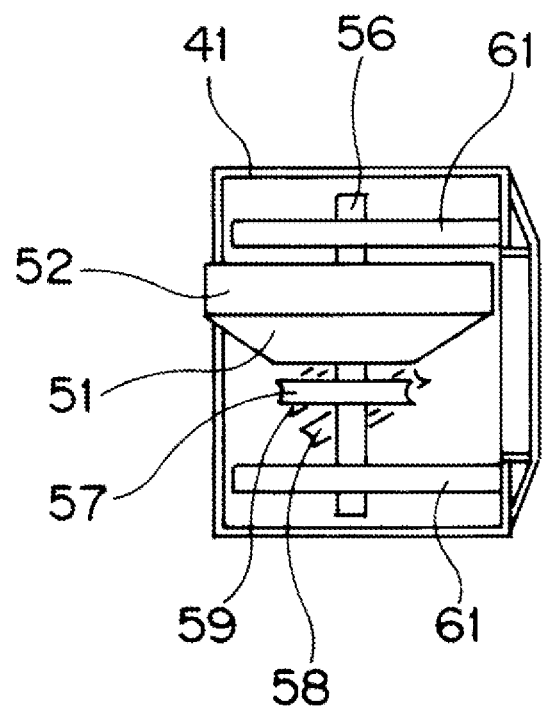
FIG. 7 is a top view of the lifting and lowering assist mechanism.

Next, the configuration of the lifting and lowering assist mechanism, which is a feature portion of the present invention, for assisting the lifting and lowering of the X-ray irradiation unit composed of the X-ray tube 44 and the collimator 45 by lifting and lowering the first lifting and lowering member 42 will be described. FIG. 5 is a side view of the lifting and lowering assist mechanism. FIG. 6 is a front view of the lifting and lowering assist mechanism. Further, FIG. 7 is a top view of the lifting and lowering assist mechanism.

The lifting and lowering assist mechanism is provided with a spiral cone pulley 51 and a winding pulley 52 connected to the spiral cone pulley 51. The spiral cone pulley 51 and the winding pulley 52 are rotatably supported at the upper portion of the support column 41 with respect to a spindle 56 provided to a pair of support plates 61 connected to the support column 41. Here, the spiral cone pulley 51 is a pulley having a conical shape in which the winding radius of a wire rope is changed by the rotation angle. The groove portion formed on the spiral cone pulley 51 which is a winding position of the wire rope is spiral in a front view.

A fixed pulley 57 is rotatably supported by the spindle 56 on which the spiral cone pulley 51 and the winding pulley 52 are rotatably supported. Below the spiral cone pulley 51, the winding pulley 52, and the fixed pulley 57, a pair of movable pulleys 58 and 59 associated with the spiral cone pulley 51, the winding pulley 52, the fixed pulley 57, and the first wire rope 54 is arranged. These movable pulleys 58 and 59 are rotatably supported by a spindle 64 provided to the movable pulley holder 63.

The first wire rope 54 is fixed, at one end thereof, to the upper plate 65 of the support column 41 by a fixing member 66. This first wire rope 54 extends downward from the upper plate 65 of the support column 41 and is sequentially wound around the movable pulley 58, the fixed pulley 57, and the movable pulley 59, and then wound around the spiral groove of the spiral cone pulley 51, and the other end is fixed to the spiral cone pulley 51 by the fixing portion 67 (see FIG. 6). Thus, as the spiral cone pulley 51 is rotated, the fixed pulley 57 and the movable pulleys 58 and 59 are rotated. When the spiral cone pulley 51, the fixed pulley 57, and the movable pulleys 58 and 59 are rotated, the movable pulleys 58 and 59 are lifted and lowered together with the movable pulley holder 63 by the action of the first wire rope 54 wound around the pulleys.

On the other hand, as described above, the second wire rope 53 is wound around the winding pulley 52. One end of the second wire rope 53 is fixed to the winding pulley 52 at a fixing portion 68 (see FIG. 6). The other end of the second wire rope 53 is fixed to the base portion 47 (see FIG. 2) arranged at the lower end portion of the first lifting and lowering member 42 as described above. As the winding pulley 52 is rotated together with the spiral cone pulley 51 and the winding amount of the second wire rope 53 by the winding pulley 52 changes, the first lifting and lowering member 42 is lifted and lowered.

A shaft 70 is provided at the lower end portion of the movable pulley holder 63. At the lower end portion of this shaft 70, a lower spring seat 75 is provided via the thrust bearing 76. For this reason, the shaft 70 is rotatable relative to the lower spring seat 75. At the lower surface of the lower plate 62 supported at the lower end portions of the pair of the support plates 61, an upper spring seat 73 is provided. Slide bearings 77 are provided between the upper spring seat 73 and the shaft 70, so the shaft 70 can slide and rotate with respect to the upper spring seat 73. Furthermore, a junction spring seat 74 is provided between the upper spring seat 73 and the lower spring seat 75. Slide bearings 77 are arranged between the junction spring seat 74 and the shaft 70, so the shaft 70 can slide and rotate relative to the junction spring seat 74.

A compression coil spring 71 is disposed between the upper spring seat 73 and the junction spring seat 74, and the compression coil spring 71 is fixed in a state in which it is in contact with the upper spring seat 73 and the junction spring seat 74. Further, a compression coil spring 72 is disposed between the junction spring seat 74 and the lower spring seat 75, and the compression coil spring 72 is fixed in a state in which it is in contact with the junction spring seat 74 and the lower spring seat 75. The shaft 70 is arranged at a position corresponding to the central axis of the compression coil springs 71 and 72. The shaft 70 does not have to be arranged at the position that coincides with the central axis of the compression coil springs 71 and 72, and may be arranged so as to face the central axis direction (up-down direction in FIG. 5 and FIG. 6) of the compression coil springs 71 and 72.

This shaft 70 functions as a coupling mechanism that couples the movable pulley holder 63 with the compression coil springs 71 and 72 in a rotatable state about an axis facing the central axis direction of the compression coil springs 71 and 72. When the movable pulley holder 63 is lifted, the compression coil springs 71 and 72 are compressed. Here, the urging force to the movable pulley holder 63 by the compression coil springs 71 and 72 increases in proportion to the amount of compression. On the other hand, the first wire rope 54 is wound around the pair of movable pulleys 58 and 59 supported by the movable pulley holder 63 and the spiral cone pulley 51. A spiral groove is formed on the spiral cone pulley 51, and as the winding amount of the first wire rope 54 with respect to the spiral cone pulley 51 increases, the distance of the winding position of the first wire rope 54 from the spindle 56 increases. As a result, regardless of the height position of the movable pulley holder 63 (i.e., the rotation angle position of the spiral cone pulley 51), the first wire rope 54 exerts the function of pulling up the base portion 47 (see FIG. 2) provided at the lower end portion of the first lifting and lowering member 42 with a constant tensile force. Therefore, when lifting and lowering the X-ray irradiation unit composed of the X-ray tube 44 and the collimator 45 supported by the second lifting and lowering member 43 via the first lifting and lowering member 42, it becomes possible to assist the lifting and lowering operation so that they can be lifted and lowered with a constant force.

Figure 8:
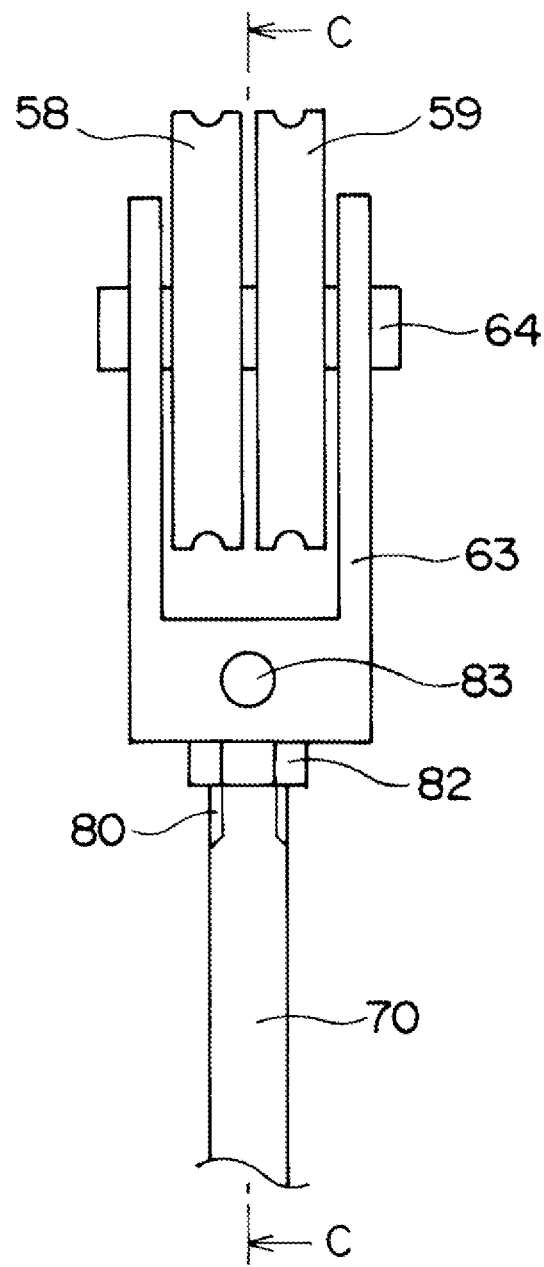
FIG. 8 is a front view of a movable pulley holder 63, etc.
Figure 9:
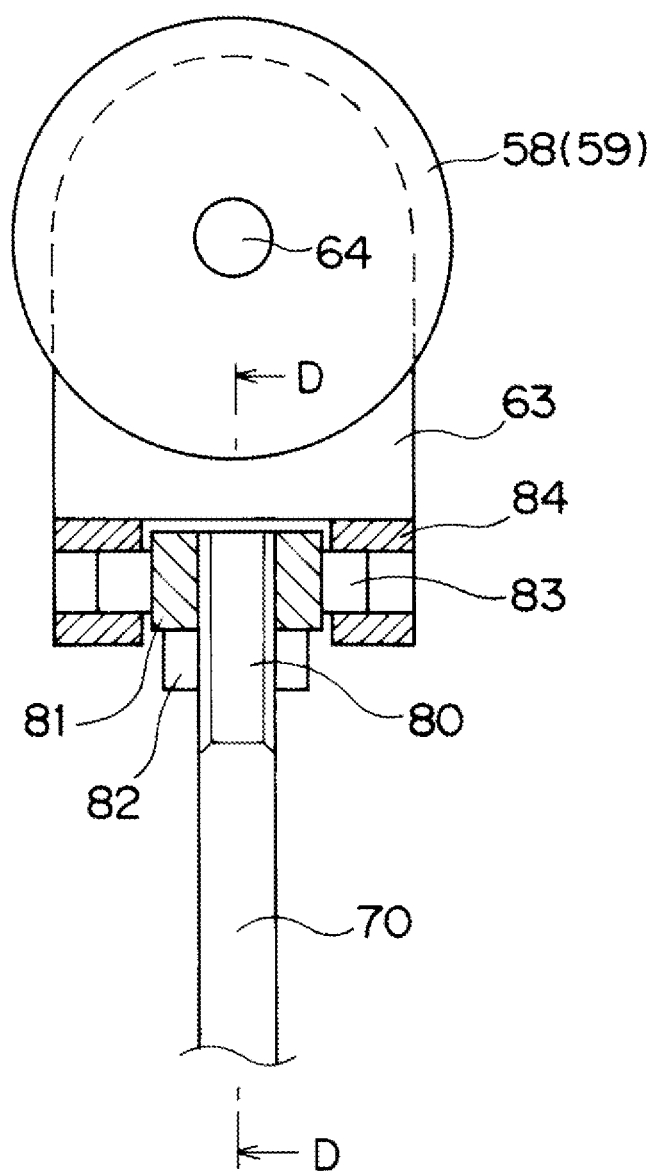
FIG. 9 is a cross-sectional view taken along the line C-C in FIG. 8.
Figure 10:
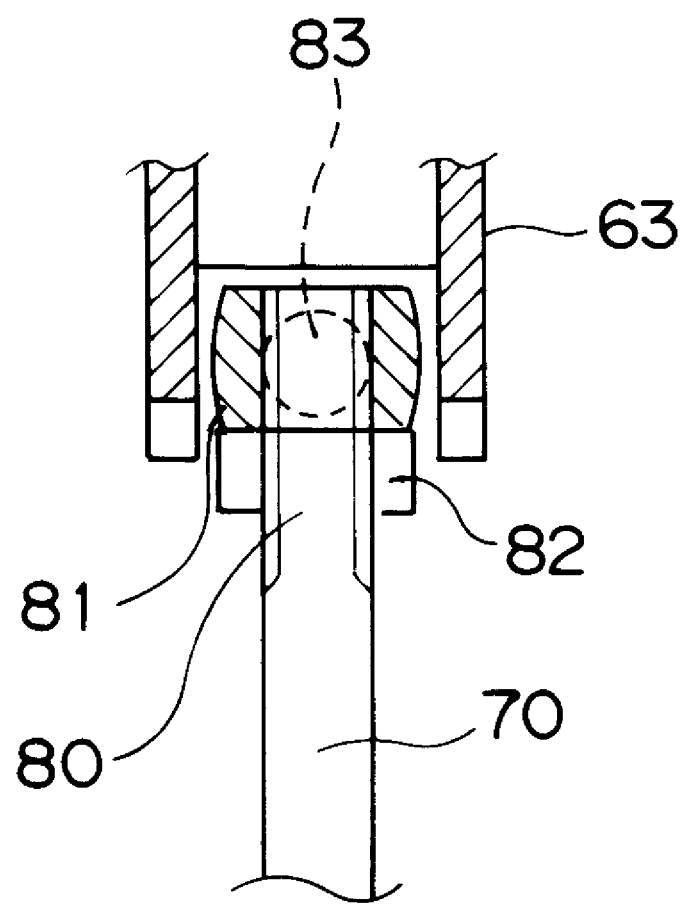
FIG. 10 is a cross-sectional view taken along the line D-D in FIG. 9.

FIG. 8 is a front view of the movable pulley holder 63, etc. FIG. 9 is a cross-sectional view taken along the line C-C in FIG. 8. FIG. 10 is a cross-sectional view taken along the line D-D in FIG. 9.

A threaded portion 80 is formed at the upper end of the shaft 70, and the threaded portion 80 is screwed to the shaft bracket 81. The threaded portion 80 of the shaft 70 is fixed to the shaft bracket 81 by the nut 82 functioning as a double nut. Shaft portions 83 are formed on both sides of the shaft bracket 81, and the shaft portions 83 are pivotally supported by hole portions formed in the lower region 84 of the movable pulley holder 63. For this reason, the movable pulley holder 63 is capable of tilting with respect to the shaft 70 about the shaft portion 83 together with the pair of movable pulleys 58 and 59. That is, the movable pulley holder 63 is configured to be tiltable together with the pair of movable pulleys 58 and 59 with respect to the shaft 70 facing the central axis direction of the compression coil springs 71 and 72.

Figure 11:
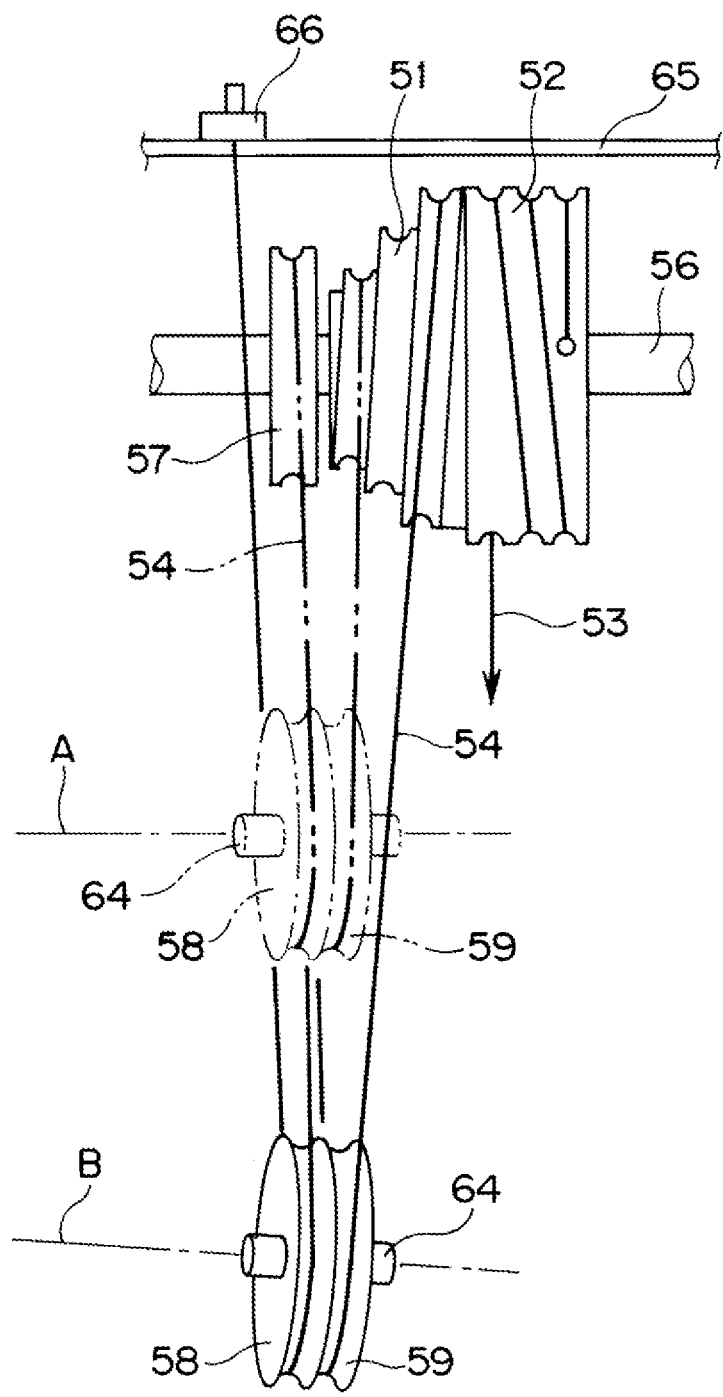
FIG. 11 is an explanatory view showing a movement operation of the movable pulleys 58 and 59 when the X-ray tube 44 and the collimator 45 are lifted and lowered.

Next, in the mobile X-ray imaging apparatus provided with the lifting and lowering assist mechanism having the above-described configuration, the lifting and lowering operation for lifting and lowering the X-ray tube 44 and the collimator 45 will be described. FIG. 11 is an explanatory view showing the movement operation of the movable pulleys 58 and 59 when the X-ray tube 44 and the collimator 45 are lifted and lowered.

As shown in FIG. 3, in a state in which the first lifting and lowering member 42 and the second lifting and lowering member 43 are lowered, the winding pulley 52 is rotated counterclockwise as viewed from the spiral cone pulley 51 side by the action of the second wire rope 53. In this state, as shown by the virtual line in FIG. 11, the first wire rope 54 wound around the movable pulley 58, the fixed pulley 57, and the movable pulley 59 in this order is wound around the spiral cone pulley 51 at the small diameter region of the spiral cone pulley 51. Therefore, the position where the first wire rope 54 wound around the fixed pulley 57 is separated from the fixed pulley 57 and the position where the first wire rope 54 wound around the spiral cone pulley 51 is separated from the spiral cone pulley 51 are close in the axial direction of the spindle 56, and the distance from the axis of the spindle 56 is also close. Thus, the axial direction A of the spindle 64 provided to the movable pulley holder 63 supporting the movable pulleys 58 and 59 is substantially parallel to the axial direction of the spindle 56 supporting the fixed pulley 57, the spiral cone pulley 51, and the winding pulley 52.

Note that in this state, the compression coil springs 71 and 72 shown in FIG. 5 and FIG. 6 are compressed, so the upper spring seat 73 and the lower spring seat 75 are positioned closer to each other than the state shown in FIG. 5 and FIG. 6.

On the other hand, as shown in FIG. 4, in a state in which the first lifting and lowering member 42 and the second lifting and lowering member 43 are lifted, the winding pulley 52 is rotated clockwise as viewed from the spiral cone pulley 51 side by the action of the second wire rope 53. In this state, as shown by the solid line in FIG. 11, the first wire rope 54 wound around the movable pulley 58, the fixed pulley 57, and the movable pulley 59 in this order is wound around the spiral cone pulley 51 at the large diameter region of the spiral cone pulley 51. For this reason, the position where the first wire rope 54 wound around the fixed pulley 57 is separated from the fixed pulley 57 and the position where the first wire rope 54 wound around the spiral cone pulley 51 is separated from the spiral cone pulley 51 are spaced apart in the axial direction of the spindle 56, and the distance from the axis of the spindle 56 is also far. For this reason, the stress to rotate the movable pulleys 58 and 59 about the axis of the shaft 70 with respect to the first wire rope 54 extending from the movable pulley 59 to the spiral cone pulley 51 and the stress to tilt the movable pulleys 58 and 59 relative to the axis of the shaft 70 occur.

However, the movable pulley holder 63 supporting the movable pulleys 58 and 59 via the spindle 64 is rotatable about the axis of the shaft 70. Therefore, at this time, the axial direction B of the spindle 64 provided to the movable pulley holder 63 supporting the movable pulleys 58 and 59 is placed at the position rotated about the axis of the shaft 70 with respect to the axial direction of the spindle 56 supporting the fixed pulley 57, the spiral cone pulley 51, and the winding pulley 52. Further, the movable pulley holder 63 supporting the movable pulleys 58 and 59 via the spindle 64 is tiltable relative to the shaft 70. Therefore, at this time, the axial direction B of the spindle 64 provided to the movable pulley holder 63 supporting the movable pulleys 58 and 59 is placed in a state of being inclined by a predetermined angle with respect to the axial direction A when the movable pulleys 58 and 59 are in the raised position. This allows the movable pulleys 58 and 59 to be automatically moved to a position at which no stress is applied to the first wire rope 54. This makes it possible to reduce the stress applied to the first wire rope 54, which in turn can prevent the shortening of the life of the first wire rope 54.

Note that in this state, the compression coil springs 71 and 72 shown in FIG. 5 and FIG. 6 are in an extended state, and the upper spring seat 73 and the lower spring seat 75 are arranged at the positions shown in FIG. 5 and FIG. 6.

When the first lifting and lowering member 42 and the second lifting and lowering member 43 are lowered together with the X-ray tube 44 and the collimator 45, the compression coil springs 71 and 72 are compressed, and the first wire rope 54 is wound around the small diameter portion of the spiral cone pulley 51. On the other hand, when the first lifting and lowering member 42 and the second lifting and lowering member 43 are lifted together with the X-ray tube 44 and the collimator 45, the compression coil springs 71 and 72 are extended, and the first wire rope 54 is wound around the large diameter portion of the spiral cone pulley 51. As a result, regardless of the height position of the movable pulleys 58 and 59, the first wire rope 54 exerts the action of pulling up the second lifting and lowering member 43 and the first lifting and lowering member 42 connected thereto via the wire rope 55 with a constant tensile force. Therefore, it becomes possible to appropriately assist the lifting and lowering operation of the X-ray irradiation unit composed of the X-ray tube 44 and the collimator 45 supported by the second lifting and lowering member 43 via the first lifting and lowering member 42.

Since the compression coil springs 71 and 72 are used to assist the lifting and lowering, even if the compression coil springs 71 and/or 72 is broken, the movable pulley holder 63 connected to the shaft 70 is moved upward by one turn of the compression coil spring 71, 72. Therefore, even in cases where the compression coil springs 71 and/or 72 is broken, it is possible to effectively prevent the first lifting and lowering member 42 and the second lifting and lowering member 43 from lowering by a great distance together with the X-ray tube 44 and the collimator 45.

In the embodiment described above, it is configured such that the first lifting and lowering member 42 is lifted and lowered by the rotation of the spiral cone pulley 51, the fixed pulley 31 is provided rotatably about the support spindle 32 fixed to the upper portion of the first lifting and lowering member 42 in order to lift and lower the second lifting and lowering member 43 by utilizing the power of lifting and lowering the first lifting and lowering member 42, and the wire rope 55 for lifting and lowering the second lifting and lowering member 43 wound around the fixed pulley 31 is provided with the one end fixed to the base portion 46 provided at the lower end portion of the support column 41 and the other end fixed to the base portion 48 provided at the lower end portion of the second lifting and lowering member 43. However, other lifting and lowering drive mechanisms, such as, e.g., racks and pinions and chains and sprockets, may be employed. Furthermore, the movement amount ratio of the first lifting and lowering member 42 and the second lifting and lowering member 43 may be other than two times.

Further, in the aforementioned embodiment, the X-ray irradiation unit composed of the X-ray tube 44 and the collimator 45 is lifted and lowered by the first lifting and lowering member 42 and the second lifting and lowering member 43. However, instead of using the first lifting and lowering member 42 and the second lifting and lowering member 43, a single lifting and lowering member or three or more lifting and lowering members may be used to lift and lower the X-ray irradiation unit by this lifting and lowering member.

In the embodiment described above, the X-ray irradiation unit composed of the X-ray tube 44 and the collimator 45 is supported by the second lifting and lowering member 43 having a substantially L-shape in a side view. However, as a support member for supporting the X-ray irradiation unit, any other shape may be used.

In the embodiment described above, although a pair of compression coil springs 71 and 72 is used, instead of the pair of compression coil springs 71 and 72, a single compression coil spring may be used. However, when using a pair of compression coil springs 71 and 72, it is possible to prevent the buckling of the springs and obtain a large stroke. Note that three or more compression coil springs may be used.

Also, in place of the compression coil springs 71 and 72, a tension spring may be used. However, as described above, when using the compression coil springs 71 and 72, even when a part of the springs is broken, it is possible to effectively prevent the first and second lifting and lowering members 42 and 43 from lowering by a great distance together with the X-ray irradiation unit.

Further, the first wire rope 54 and the second wire rope 53 in the above-described embodiment may be respectively configured by two wire ropes to prevent lowing.

In the embodiment described above, the pair of movable pulleys 58 and 59 and the fixed pulley 57 are used, but it may be configured such that one movable pulley is used and the fixed pulley 57 is omitted. However, when multiple movable pulleys and a fixed pulley are used, it is possible to make the lifting and lowering stroke of the X-ray irradiation unit composed of the X-ray tube 44 and the collimator 45 larger than the stroke of the compression coil springs 71 and 72.

Furthermore, the LCD touch panel 22 may not be provided as a display unit. The X-ray detector 24 may not necessarily be a flat panel detector, such as, e.g., an X-ray film and a sheet using a stimulable phosphor.

DESCRIPTION OF REFERENCE SYMBOLS

1: main body
2: body
3: chassis
11: front wheel
12: rear wheel
31: fixed pulley
41: support column
42: first lifting and lowering member
43: second lifting and lowering member
44: X-ray tube
45: collimator
51: spiral cone pulley
52: winding pulley
53: second wire rope
54: first wire rope
55: wire rope
56: spindle
57: fixed pulley
58: movable pulley
59: movable pulley
63: movable pulley holder
64: spindle
70: shaft
71: compression coil spring
72: compression coil spring
73: upper spring seat
74: junction spring seat
75: lower spring seat
76: thrust bearing
77: slide bearing
80: threaded portion
81: shaft bracket
83: shaft portion

The invention claimed is:

1. A mobile radiographic imaging apparatus provided with a main body with wheels, a support column erected on the main body, and a lifting and lowering member configured to be lifted and lowered along the support column in a state of supporting a radiation irradiation portion, the mobile radiographic imaging apparatus comprising:

a lifting and lowering assist mechanism including a spiral cone pulley in which a winding radius of a wire rope changes depending on a rotation angle, the spiral cone pulley being provided at an upper portion of the support column in a rotatable manner, a movable pulley, and a wire rope wound around the movable pulley and the spiral cone pulley with one end of the wire rope fixed to the support column and the other end thereof fixed to the spiral cone pulley;

a movable pulley holder configured to support a rotary spindle of the movable pulley;

a spring configured to apply tension to the wire rope;

a coupling mechanism configured to couple the movable pulley holder with the spring in a manner as to be rotatable about an axis facing a central axis direction of the spring; and a lifting and lowering drive mechanism configured to lift and lower the lifting and lowering member by rotation of the spiral cone pulley, wherein the lifting and lowering assist mechanism is configured to change a rotation angle of the movable pulley holder according to the winding amount of the wire rope wound around the spiral cone pulley.

2. The mobile radiographic imaging apparatus as recited in claim 1, wherein the lifting and lowering drive mechanism includes:

a winding pulley that rotates in synchronization with the spiral cone pulley; and a second wire rope wound around the winding pulley with one end of the second wire rope fixed to the winding pulley and the other end thereof fixed to the lifting and lowering member.

3. A mobile radiographic imaging apparatus provided with a main body with wheels, a support column erected on the main body, and a lifting and lowering member configured to be lifted and lowered along the support column in a state of supporting a radiation irradiation portion, the mobile radiographic imaging apparatus comprising:

a spiral cone pulley in which a winding radius of a wire rope changes depending on a rotation angle, the spiral cone pulley being provided at an upper portion of the support column in a rotatable manner;

a movable pulley;

a wire rope wound around the movable pulley and the spiral cone pulley with one end of the wire rope fixed to the support column and the other end thereof fixed to the spiral cone pulley;

a movable pulley holder configured to support a rotary spindle of the movable pulley;

a spring configured to apply tension to the wire rope;

a coupling mechanism configured to couple the movable pulley holder with the spring in a manner as to be rotatable about an axis facing a central axis direction of the spring; and a lifting and lowering drive mechanism configured to lift and lower the lifting and lowering member by rotation of the spiral cone pulley, wherein the movable pulley holder is configured to be tiltable with respect to an axis facing the central axis direction of the spring.

4. The mobile radiographic imaging apparatus as recited in claim 3, wherein the lifting and lowering drive mechanism includes:

a winding pulley that rotates in synchronization with the spiral cone pulley; and a second wire rope wound around the winding pulley with one end of the second wire rope fixed to the winding pulley and the other end thereof fixed to the lifting and lowering member.

5. A mobile radiographic imaging apparatus provided with a main body with wheels, a support column erected on the main body, and a lifting and lowering member configured to be lifted and lowered along the support column in a state of supporting a radiation irradiation portion, the mobile radiographic imaging apparatus comprising:

a spiral cone pulley in which a winding radius of a wire rope changes depending on a rotation angle, the spiral cone pulley being provided at an upper portion of the support column in a rotatable manner;

a movable pulley;

a wire rope wound around the movable pulley and the spiral cone pulley with one end of the wire rope fixed to the support column and the other end thereof fixed to the spiral cone pulley;

a movable pulley holder configured to support a rotary spindle of the movable pulley;

a spring configured to apply tension to the wire rope;

a coupling mechanism configured to couple the movable pulley holder with the spring in a manner as to be rotatable about an axis facing a central axis direction of the spring; and a lifting and lowering drive mechanism configured to lift and lower the lifting and lowering member by rotation of the spiral cone pulley, wherein the spring is a compression coil spring with an upper end fixedly in contact with an upper spring seat provided at a holding member, and wherein the coupling mechanism is provided with a shaft that couples a lower spring seat in contact with a lower end of the compression coil spring and the movable pulley holder.

6. The mobile radiographic imaging apparatus as recited in claim 5, wherein the lifting and lowering drive mechanism includes:

a winding pulley that rotates in synchronization with the spiral cone pulley; and a second wire rope wound around the winding pulley with one end of the second wire rope fixed to the winding pulley and the other end thereof fixed to the lifting and lowering member.

* * * * *